(12) United States Patent
Welsh et al.

(10) Patent No.: US 8,569,350 B2
(45) Date of Patent: Oct. 29, 2013

(54) ANTI-MITOTIC ANTI-PROLIFERATIVE COMPOUNDS

(75) Inventors: William J. Welsh, Princeton, NJ (US); Youyi Peng, Somerset, NJ (US); Xin Wang, Piscataway, NJ (US); Susan M. Keenan, Longmont, CO (US); Qiang Zhang, Piscataway, NJ (US); Sonia Arora, Franklin Park, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/403,617

(22) Filed: Feb. 23, 2012

(65) Prior Publication Data

US 2012/0149744 A1     Jun. 14, 2012

Related U.S. Application Data (62) Division of application No. 11/577,953, filed as application No. PCT/US2005/038655 on Oct. 25, 2005, now Pat. No. 8,143,299.

(60) Provisional application No. 60/666,944, filed on Mar. 31, 2005, provisional application No. 60/621,722, filed on Oct. 25, 2004.

(51) Int. Cl.
*A61K 31/4196*   (2006.01)
*C07D 249/08*   (2006.01)

(52) U.S. Cl.
USPC ......... 514/383; 548/255; 548/262.2; 514/359

(58) Field of Classification Search
USPC ..................... 548/255, 262.2; 514/359, 383
See application file for complete search history.

(56) References Cited

U.S. PATENT DOCUMENTS 8,143,299 B2 *   3/2012   Welsh et al. .................. 514/383

FOREIGN PATENT DOCUMENTS

EP   0155486 A1   9/1985

OTHER PUBLICATIONS

Asker, et al. "Action of Organomagnesium Compounds, Piperidine, and Aromatic Thiols on 4-Arylazo-2-phenyloxazolin-5-ones". J. Org. Chem. 26 (5): 1440-1443. (1960). Abstract only.

Szilagyi, et al. Preparation and antiarthritic activity of new 1,5-diaryl-3-alkylthio-1H-1,2,4-triazoles and corresponding sulfoxides and sulfones. Eur. J. Med. Chem. 25(2): 95-101. (1990) Abstract only.

* cited by examiner

*Primary Examiner* — Golam M M Shameem
(74) *Attorney, Agent, or Firm* — Fox Rothschild LLP (57) ABSTRACT

Substituted triazole compounds and pharmaceutical compositions thereof are presented. Also presented are methods for treating a pathology linked to a hyperproliferative disorder by administering the substituted triazole compounds to a patient in need thereof.

17 Claims, 4 Drawing Sheets

Figure 1. Anti-tubulin Activity (μM) and Cytotoxicity (nM) of T111-T116

| | Anti-tubulin $IC_{50}$ (μM) | Cytotoxicity (nM) | | | | |
|---|---|---|---|---|---|---|
| | | Cervix | colon | Breast | cervix | |
| | | HeLa | HCT-116 | ZR-75-1 | KB-3-1 | KB-V1 |
| T111 | ND* | 290 | 230 | 522 | 373 | 907 |
| T112 | 4.1 | 29.6 | 91.5 | 308 | 119 | 323 |
| T113 | 6.0 | 25 | 88.9 | 141 | 57.3 | 3333 |
| T114 | ND | 173 | 365 | 367 | 399 | 1479 |
| T115 | 3.0 | 8.73 | 7.39 | 23.8 | 9.9 | 20.8 |
| T116 | 5.6 | 18.0 | 24.3 | ND | 15.0 | 32.1 |
| CA-4 | 5.8 | 0.30 | 0.35 | 0.24 | 0.78 | 0.64 |
| Colchicine | ND | 1.84 | 2.75 | 3.41 | 3.99 | 620 |
| Paclitaxel | ND | ND | ND | 15 | 23.3 | >10000 |

*: Not determined.

Figure 2. Drug like properties of triazole compounds

| Compound | Molecular Weight | Number of Rings | Rotatable Bonds | H-Bond Acceptors | H-Bond Donors | *ClogP* |
|---|---|---|---|---|---|---|
| T111 | 341.4 | 3 | 8 | 7 | 0 | 2.60 |
| T112 | 354.5 | 3 | 9 | 7 | 0 | 2.89 |
| T113 | 357.4 | 3 | 9 | 8 | 1 | 1.97 |
| T114 | 359.4 | 3 | 8 | 8 | 0 | 2.56 |
| T115 | 364.4 | 4 | 7 | 7 | 0 | 3.06 |

Figure 3. Cytotoxicities of T115 in drug resistant cancer cell lines and cell line from normal tissue

| Origin | Cell Line | IC50 (nM) |
|---|---|---|
| Breast (parental) | MCF-7 | 4.3 |
| Breast (MDR+) | MCF-7-Adr | 12.8 |
| Breast (MDR+) | BC-19 | 3.2 |
| Ovarian (parental) | A2780 | 21.1 |
| Ovarian (MDR+) | A2780-DX | 23.82 |
| Cervix (parental) | KB-3-1 | 9.9 |
| Cervix (MRP+) | KB-4-D-10 | 5.7 |
| Cervix (MDR+) | KB-V1 | 20.8 |
| Prostate (parental) | PC-3 | 2s0.3 |
| Prostate (MRP+) | PC-3-Adr | 24.4 |
| Leukemia (parental) | P388S | 2.1 |
| Leukemia (MDR+) | P388-VMDRC | 2.3 |
| Normal | GM05659 | >10000 |

Figure 4. Growth Inhibition ($\log_{10}GI_{50}$) of Cancer Cell Lines by Compounds T111-T115

| Cell Line | T111 | T112 | T113 | T114 | T115 | | Cell Line | T111 | T112 | T113 | T114 | T115 |
|---|---|---|---|---|---|---|---|---|---|---|---|---|
| Leukemia | | | | | | | CNS Cancer | | | | | |
| CCRF-CEM | -5.73 | -7.21 | -6.53 | -5.59 | -7.49 | | SF-268 | -5.23 | -7.46 | -6.59 | -5.03 | <-8.00 |
| HL-60(TB) | -5.39 | -6.98 | -6.41 | -5.22 | -7.38 | | SF-295 | -5.89 | -7.43 | -6.52 | -5.73 | <-8.00 |
| K-562 | -6.20 | -7.89 | -6.68 | -6.12 | -7.83 | | SF-539 | -5.39 | -6.49 | -6.43 | -5.41 | <-8.00 |
| Non-Small Cell Lung Cancer | | | | | | | SNB-19 | -5.28 | -6.69 | -6.39 | -5.20 | -7.35 |
| A549/ATCC | -5.08 | -6.40 | -6.00 | -4.92 | -7.43 | | SNB-75 | -5.63 | -6.97 | -6.60 | -5.52 | -7.89 |
| EKVX | -4.43 | >-4.00 | n/a | -4.05 | <-8.00 | | U251 | -5.36 | -6.82 | -6.39 | -5.29 | -7.48 |
| HOP-62 | -5.68 | -6.56 | -6.31 | -5.69 | -7.73 | | Melanoma | | | | | |
| HOP-92 | >-4.00 | -6.41 | -6.21 | -5.27 | -7.08 | | LOX IMVI | -5.36 | -6.66 | -6.26 | -5.29 | -7.25 |
| NCI-H226 | -5.28 | -4.00 | >-4.00 | -5.15 | -4.07 | | M14 | -5.71 | -7.30 | -6.53 | 5.65 | -7.73 |
| NCI-H23 | -5.50 | -5.17 | -5.37 | -5.65 | -7.34 | | SK-MEL-2 | n/a | n/a | -6.14 | n/a | -6.78 |
| NCI-H322M | -5.25 | -5.58 | -4.04 | -5.09 | <-8.00 | | SK-MEL-28 | -5.02 | n/a | -6.37 | -4.40 | <-8.00 |
| NCI-H460 | -5.47 | -6.75 | -6.39 | -5.50 | -7.48 | | SK-MEL-5 | -5.62 | -7.16 | -6.54 | -5.59 | -7.85 |
| NCI-H522 | n/a | -7.24 | -6.58 | -5.34 | <-8.00 | | UACC-257 | -5.40 | -4.00 | >-4.00 | i | -6.61 |
| Colon Cancer | | | | | | | UACC-62 | -5.49 | -7.02 | -6.39 | -5.44 | <-8.00 |
| COLO 205 | -5.46 | -7.06 | -5.93 | -5.40 | -7.54 | | Renal Cancer | | | | | |
| HCC-2998 | -6.53 | -7.07 | -6.03 | -6.20 | -7.62 | | 786-0 | -5.60 | -6.40 | -6.30 | -5.50 | -7.49 |
| HCT-116 | -5.52 | -7.22 | -6.40 | -5.52 | -7.51 | | A498 | -5.42 | -6.31 | -6.38 | -5.09 | -7.80 |
| HCT-15 | -5.77 | -7.22 | -6.20 | -5.78 | -7.45 | | ACHN | -5.35 | -6.69 | -6.29 | -5.25 | -7.46 |
| HT29 | -5.67 | -7.51 | -5.54 | -5.50 | -7.64 | | CAK1-1 | -5.59 | -6.87 | -6.15 | -5.53 | <-8.00 |
| KM12 | -5.67 | -7.58 | -6.85 | -5.84 | <-8.00 | | RXF 393 | -5.80 | -5.79 | -6.51 | -5.77 | <-8.00 |
| SW-620 | -5.56 | -7.12 | -6.42 | -5.39 | -7.47 | | SN12C | -5.39 | -6.14 | -6.22 | -5.33 | -7.20 |
| Ovarian Cancer | | | | | | | TK-10 | -5.01 | -5.78 | -5.13 | >-4.00 | <-8.00 |
| IGROV1 | n/a | -7.02 | -6.35 | -5.31 | -7.45 | | UO-31 | n/a | -6.02 | -6.30 | -4.75 | -7.49 |
| OVCAR-3 | -5.76 | -7.46 | -6.71 | -5.68 | <-8.00 | | Breast Cancer | | | | | |
| OVCAR-4 | -5.26 | -4.68 | -6.38 | -5.28 | -5.98 | | MCF7 | -5.77 | -6.56 | -6.21 | -6.00 | -7.36 |
| OVCAR-5 | -5.42 | -5.37 | -5.71 | -5.25 | -7.32 | | NCI/ADR—RES | -5.75 | -6.89 | -5.81 | -5.70 | -7.68 |
| OVCAR-8 | -5.32 | -5.59 | -6.01 | -5.20 | -7.37 | | MDA-MB-231/ATCC | -5.50 | -5.99 | -6.01 | -5.19 | -7.51 |
| Prostate Cancer | | | | | | | HS 578T | -5.53 | -6.38 | -6.44 | -5.19 | -7.79 |
| PC-3 | -5.31 | -7.55 | -6.54 | -5.52 | -7.71 | | MDA-MB-435 | -6.63 | <-8.00 | -7.61 | -6.48 | <-8.00 |
| DU-145 | -5.53 | -5.73 | -6.18 | -5.32 | <-8.00 | | BT-549 | -5.01 | -4.60 | -5.44 | -5.03 | -7.43 |
| | | | | | | | T-47D | n/a | -7.32 | -6.57 | >-4.00 | -7.35 |

ANTI-MITOTIC ANTI-PROLIFERATIVE COMPOUNDS

CROSS-REFERENCE TO RELATED APPLICATIONS

This application is a Divisional of granted U.S. patent application Ser. No. 11/577,953, which has a 35 U.S.C. §371 (c) filing date of Sep. 9, 2009, and which is the U.S. National Stage filing of International patent application Ser. No. PCT/US05/38655, which was filed Oct. 25, 2005, and which claims priority under 35 U.S.C. §119(e) to U.S. Provisional Patent Application Ser. No. 60/666,944, which was filed on Mar. 31, 2005, and U.S. Provisional Patent Application Ser. No. 60/621,722, which was filed on Oct. 25, 2004. The disclosures of the foregoing applications are incorporated herein by reference in their entireties.

BACKGROUND OF THE INVENTION

Cancers are regarded as one of the most common human diseases in the world. According to the statistical data released by WHO (World Health Organization), more than 10 million people are diagnosed with cancer every year and 6 million people (representing 12% of deaths worldwide) die as a result of this deadly disease. Moreover, global cancer rates are projected to increase by 50% to 15 million by 2020. Although tremendous advances have been made in the understanding of the molecular pathology of malignant tumors, progress in the development of novel anti-cancer drugs has remained slow.

Cancer therapies attempt to exploit differences between malignant tumor cells and normal cells and often take advantage of major distinctions within cell-cycle control mechanisms. As compared to the majority of normal somatic cells that are in a quiescent phase of cell cycle, cancer cells undergo a much faster and more disorganized cell cycle. Mitosis is a stage of the cell cycle in which the microtubule system plays a crucial role. Disruption of the microtubule spindle formation either by inhibiting polymerization or preventing depolymerization of tubulin results in cell-cycle arrest and cell death. Therefore, the microtubule system of eukaryotic cells is widely regarded as a potent drug target for the development of anti-cancer therapeutic agents. The α- and β-tubulin heterodimer is the building block of microtubules and, as such, is the biochemical target for several clinically used chemotherapeutics. Tubulin binding compounds which interfere with the dynamic stability of microtubules and disrupt the formation of mitotic spindles are widely considered one of the most desirable classes of anti-cancer agents. Indeed, great commercial success has been achieved by paclitaxel, a small-molecule microtubule stabilizer.

Clinically used compounds which interfere with microtubule dynamics usually bind to one of three major binding sites named after representative inhibitory ligands: taxane, vinca alkaloid, and colchicines. However, these clinically used anti-tubulin drugs often face limitations such as neural and systemic toxicity, poor water solubility and bioavailability, and complex synthetic pathways and isolation procedures. Moreover, these clinically-used antimitotic drugs suffer from negative side effects such as the development of peripheral neurotoxicity and the induction of various drug resistance mechanisms. For example, P-gP (P-glucoprotein) and MRP (Multidrug Resistance Protein) are both efflux pumps that expel foreign toxicants from cells to reduce or even eliminate cytotoxicity as a result of decreased intracellular drug concentrations. Furthermore, existing chemotherapeutic agents have complex synthetic pathways and are often difficult to isolate.

Colchicine was one of the first natural anti-mitotic drugs to be investigated. It binds to a single site in β-tubulin and destroys mitotic spindle formation by inhibiting tubulin polymerization. However, colchicine treatment results in high cytotoxicity and multiple side effects.

Combretastatin A-4 (CA-4) is a potent tubulin polymerization inhibitor with one of the simplest chemical structures. It has a broad spectrum of activity. Moreover, it cannot be recognized by the multidrug resistance (MDR) pump. Association with the MDR results in drug resistance as drugs and other foreign molecules are rapidly ejected from the cytoplasm. CA-4 has also been reported to inhibit tumor growth by disrupting angiogenesis. Unfortunately, the structural instability of the cis-double bond of CA-4 has limited the compound's in vivo efficacy.

Therefore, a need exists for novel anti-mitotic compounds that exhibit fewer side effects, have higher anti-tubulin activity, and which are easily synthesized and isolated.

SUMMARY OF THE INVENTION

This need is met by the present invention, which relates to a compound of Formula I:

wherein

Het is a substituted 1,2,4-triazole or 1,2,3-triazole;

$Z_1$, $Z_2$, and $Z_3$ are independently a bond or $R_1$—X—$R_2$, wherein X is $NR_3$, O, S, SO, or $SO_2$; $R_1$ and R2 are independently a bond or substituted or unsubstituted, saturated or unsaturated, straight-chained or branched lower alkylene; and $R_3$ is hydrogen, substituted or unsubstituted phenyl, or substituted or unsubstituted, saturated or unsaturated, straight-chained or branched lower alkyl;

$Ar_1$ and $Ar_2$ are independently substituted or unsubstituted monocyclic aryl, or heteroaryl ring systems of 5 or 6 ring atoms or bicyclic aryl or heteroaryl ring systems of 8 to 12 ring atoms, wherein each monocyclic ring may contain 0 to 3 heteroatoms, each bicyclic ring may contain 0 to 4 heteroatoms, and each heteroatom is independently selected from the group consisting of N, O, and S;

$R_a$ is hydrogen or substituted or unsubstituted monocyclic aryl, or heteroaryl ring systems of 5 or 6 ring atoms or bicyclic aryl or heteroaryl ring systems of 8 to 12 ring atoms, wherein each monocyclic ring may contain 0 to 3 heteroatoms, each bicyclic ring may contain 0 to 4 heteroatoms, and each heteroatom is independently selected from the group consisting of N, O, and S; and the substituents of $Ar_1$, $Ar_2$, and $R_a$, when substituted, comprise one to three moieties independently selected from the group consisting of alkyl, alkenyl, alkynyl, phenyl, aralkyl, aralkenyl, hydroxy, hydroxyalkyl, alkoxy, alkoxyalkyl, aralkoxy, aryloxy, acyloxy, halo, haloalkyl, nitro, cyano, amino, mono- and dialkylamino, acylamino, carboxy, carboxyalkyl, carbalkoxy, carbaralkoxy, carbalkoxyalkyl, carbalkoxyalkenyl, aminoalkoxy, amido, mono-alkylamido, di-alkylamido, N,N-cycloalkylamido, sulfonyl, mono-alkyl sulfonyl, di-alkyl sulfonyl, sulfamoyl, mono-alkyl sulfamoyl, di-alkyl sulfamoyl, halophenyl, benzoyl, alkylthio and alkylsulfinyl; or a hydrate thereof, solvate thereof, prodrug thereof or pharmaceutically acceptable salt thereof;

provided that when Het is a 1,2,4-triazole $Z_1$, $Z_2$, and $Z_3$ are each a bond; $R_a$ is a hydrogen at position 3 of the triazole; $Ar_1$ is a 3,4,5-trimethoxyphenyl at position 4 of the triazole; and $Ar_2$ is a substituted benzene at position 5 of the triazole; then $Ar_2$ is substituted with other than the combination of a nitro and an amino group.

Another aspect of the invention is a pharmaceutical composition comprising a pharmaceutically effective amount of the compound of the present invention and a pharmaceutically acceptable carrier.

Another aspect of the present invention provides a method for treating a pathology linked to a hyperproliferative disorder by administering to a patient in need thereof an anti-mitotic effective amount of the compound of the present invention. One embodiment of this aspect of the present invention provides a method of treating or preventing restenosis in a patient by administering a pharmaceutically effective amount of the compound of the present invention at a predetermined site.

An additional aspect of the invention provides a method for treating inflammation in a patient by administering an effective amount of the compound of the present invention.

Another aspect of the present invention provides a stent device coated with an anti-mitotic effective amount of the compound of the present invention.

BRIEF DESCRIPTION OF THE DRAWINGS

FIG. 4 is a table demonstrating the growth inhibition (log 10GI50) of cancer cell lines by compounds T111-T115.

DETAILED DESCRIPTION OF THE INVENTION

The present invention relates to substituted 1,2,4-triazole and 1,2,3-triazole compounds. Also disclosed are methods of treating a patient by administering the triazole compounds.

As used above, and throughout the description of the invention, the following terms, unless otherwise indicated, shall be understood to have the following meanings:

"Patient" means a mammal including a human.

"Effective amount" means an amount of compound of the present invention effective in inhibiting cellular mitosis, and thus producing the desired therapeutic effect.

"Alkyl" means aliphatic hydrocarbon group which may be branched or straight-chained having about 1 to about 10 carbon atoms. Preferred alkyl is "lower alkyl" having about 1 to about 3 carbon atoms; more preferred is methyl. Branched means that one or more lower alkyl groups such as methyl, ethyl, or propyl are attached to a linear alkyl chain. The alkyl group is also optionally substituted by alkoxy, halo, carboxy, hydroxy or $R_4R_5N$— (wherein $R_4$ and $R_5$ are independently hydrogen or alkyl, or $R_4$ and $R_5$ taken together with the nitrogen atom to which $R_4$ and $R_5$ are attached form azaheterocyclyl); and preferably optionally substituted by fluoro. Examples of alkyl include methyl, fluoromethyl, difluoromethyl, trifluoromethyl, ethyl, n-propyl, isopropyl, butyl, sec-butyl, t-butyl, amyl and hexyl.

"Cycloalkyl" means a non-aromatic monocyclic ring system of about 3 to about 7 carbon atoms. Preferred monocyclic cycloalkyl rings include cyclopentyl, cyclohexyl, and cycloheptyl; more preferred are cyclohexyl and cyclopentyl.

"Aryl" means aromatic carbocyclic radical containing about 6 to about 10 carbon atoms. Exemplary aryl include phenyl or naphthyl, or phenyl or naphthyl substituted with one or more aryl group substituents which may be the same or different, where "aryl group substituent" includes hydrogen, hydroxy, halo, alkyl, alkoxy, carboxy, alkoxycarbonyl or $Y_1Y_2NCO$—, wherein $Y_1$ and $Y_2$ are independently hydrogen or alkyl.

"Heteroaryl" means about a 5- to about a 10-membered aromatic monocyclic or bicyclic hydrocarbon ring system in which one to three of the atoms in a monocyclic ring system, and one to four of the atoms in a bicyclic ring system, is/are elements(s) other than carbon, for example nitrogen, oxygen or sulfur. The "heteroaryl" may also be substituted by one or more of the above-mentioned "aryl group substituents". Exemplary heteroaryl groups include substituted pyrazinyl, furanyl, thienyl, pyridyl, pyrimidinyl, isoxazolyl, isothiazolyl, oxazolyl, thiazoly, pyrazolyl, furazanyl, pyrrolyl, imidazo[2,1-b]thiazolyl, benzofurzanyl, indolyl, azaindolyl, benzimidazolyl, benzothienyl, quinolinyl, imidazolyl and isoquinolinyl.

"Acyl" means an H—CO— or alkyl-CO— group in which the alkyl group is as previously described. Preferred acyls contain a lower alkyl. Exemplary acyl groups include formyl, acetyl, propanoyl, 2-methylpropanoyl, butanoyl and caproyl.

"Alkoxy" means an alkyl-O— group in which the alkyl group is as previously described. Preferred alkoxy is "lower alkoxy" having about 1 to about 3 carbon atoms; more preferred is methoxy. The alkoxy may be optionally substituted by one or more alkoxy, carboxy, alkoxycarbonyl, carboxyaryl or $R_4R_5N$— (wherein $R_4$ and $R_5$ are as defined above). Exemplary alkoxy groups include methoxy, ethoxy, n-propoxy, i-propoxy, n-butoxy, heptoxy, 2-(morpholin-4-yl)ethoxy and 2-(ethoxy)ethoxy.

"Aryloxy" means aryl-O— group in which the aryl group is as previously described.

"Acyloxy" means and acyl-O— group in which the acyl group is as previously described.

"Carboxy" means a HO(O)C— (carboxylic acid) group.

"$R_4R_5N$—" means a substituted or unsubstituted amino group, wherein $R_4$ and $R_5$ are as previously described. Exemplary groups include amino ($H_2N$—), methylamino, ethylmethylamino, dimethylamino and diethylamino.

"$R_4R_5NCO$—" means a substituted or unsubstituted carbomoyl group, wherein $R_4$ and $R_5$ are as previously described. Exemplary groups are carbamoyl ($H_2N\,CO$—) are dimethylaminocarbamoyl ($Me_2NCO$—).

"Acyl$R_4N$—" means an acylamino group wherein $R_4$ and acyl are as defined herein.

"Halo" means fluoro, chloro, bromo, or iodo. Preferred are fluoro, chloro or bromo, and more preferred are fluoro or chloro.

"Prodrug" means a form of the compound of formula I suitable for administration to a patient without undue toxicity, irritation, allergic response, and the like, and effective for their intended use. A prodrug is transformed in vivo to yield the parent compound of the above formula, for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, et., Bioreversible Carriers in Drug Design, American Pharmaceutical Association and Pergamon Press, 1987, both of which are incorporated herein by reference.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like. "Hydrate" is a solvate wherein the solvent molecule(s) is/are $H_2O$.

"Substituted 1,2,4-triazole" means the formula:

wherein positions 3, 4, and 5 are independently substituted; or the formula:

wherein positions 1, 3, and 5 are independently substituted.

"Substituted 1,2,3-triazole" means the formula:

wherein positions 2, 4, and 5 are independently substituted.

One embodiment of the present invention is a compound of formula I wherein $Ar_1$ and $Ar_2$ are independently substituted or unsubstituted benzene, pyrrole, thiophene, furan, thiazole, imidazole, pyrazole, 1,2,4-triazole, pyridine, 2(1H)-pyridone, 4(1H)-pyridone, pyrazine, pyrimidine, pyridazine, isothiazole, isoxazole, oxazole, tetrazole, naphthalene, tetralin, naphthyridine, benzofuran, benzothiophene, indole, 2,3-dihydroindole, 1H-indazole, indoline, benzopyrazole, 1,3-benzodioxole, benzoxazole, purine, coumarin, chromone, quinoline, tetrahydroquinoline, isoquinoline, benzimidazole, quinazoline, pyrido[2,3-b]pyrazine, pyrido[3,4-b]pyrazine, pyrido[3,2-c]pyridazine, pyrido[3,4-b]-pyridine, 1H-pyrazole[3,4-d]pyrimidine, pteridine, 2(1H)-quinolone, 1(2H)-isoquinolone, 1,4-benzisoxazine, benzothiazole, quinoxaline, quinoline-N-oxide, isoquinoline-N-oxide, quinoxaline-N-oxide, quinazoline-N-oxide, benzoxazine, phthalazine, or cinnoline.

Another embodiment of the present invention is a compound of formula I, wherein wherein $R_a$ is substituted or unsubstituted benzene, pyrrole, thiophene, furan, thiazole, imidazole, pyrazole, 1,2,4-triazole, pyridine, 2(1H)-pyridone, 4(1H)-pyridone, pyrazine, pyrimidine, pyridazine, isothiazole, isoxazole, oxazole, tetrazole, naphthalene, tetralin, naphthyridine, benzofuran, benzothiophene, indole, 2,3-dihydroindole, 1H-indazole, indoline, benzopyrazole, 1,3-benzodioxole, benzoxazole, purine, coumarin, chromone, quinoline, tetrahydroquinoline, isoquinoline, benzimidazole, quinazoline, pyrido[2,3-b]pyrazine, pyrido[3,4-b]pyrazine, pyrido[3,2-c]pyridazine, pyrido[3,4-b]-pyridine, 1H-pyrazole[3,4-d]pyrimidine, pteridine, 2(1H)-quinolone, 1(2H)-isoquinolone, 1,4-benzisoxazine, benzothiazole, quinoxaline, quinoline-N-oxide, isoquinoline-N-oxide, quinoxaline-N-oxide, quinazoline-N-oxide, benzoxazine, phthalazine, or cinnoline.

Another embodiment of the present invention is a compound of formula I, wherein Het is a substituted triazole; each of $Z_i$, $Z_2$, and $Z_3$ is a bond; $Ar_1$ and $Ar_2$ are each a substituted benzene; and $R_a$ is hydrogen.

Another embodiment of the present invention are compounds of formula I, wherein $Ar_1$ and $Ar_e$ are each substituted with 1 to 3 alkoxy groups. Species of this embodiment include compounds of formula I, wherein $Ar_1$ and $Ar_2$ are each benzene rings substituted with 1 to 3 alkoxy groups.

Another embodiment of the present invention are compounds of formula I, wherein $Ar_1$ and $Ar_2$ are each substituted with 1 to 3 trifluoromethoxy groups. Species of this embodiment include compounds of formula I, wherein $Ar_1$ and $Ar_2$ are each benzene rings substituted with 1 to 3 trifluoromethoxy groups. Yet another embodiment of the present invention are compounds of formula I, wherein $Ar_1$ is substituted with 1 to 3 alkoxy groups and $Ar_2$ is substituted with a dialkylamino group. Species of this embodiment include compounds of formula I, wherein $Ar_1$ is a benzene ring substituted with 1 to 3 alkoxy groups and $Ar_2$ is a benzene ring substituted with a dialkylamino group.

Another embodiment of the present invention are compounds of formula I, wherein $Ar_1$ is substituted with 1 to 3 alkoxy groups and $Ar_2$ is substituted with a hydroxyl group and an alkoxy group. Species of this embodiment include compounds of formula I, wherein $Ar_1$ is a benzene ring substituted with 1 to 3 alkoxy groups and $Ar_2$ is a benzene ring substituted with a hydroxyl group and an alkoxy group.

Another embodiment of the present invention are compounds of formula I, wherein $A_1$ is substituted with 1 to 3 alkoxy groups and $Ar_2$ is substituted with a halogen and an alkoxy group. Species of this embodiment include compounds of formula I, wherein $Ar_1$ is a benzene ring substituted with 1 to 3 alkoxy groups and $Ar_2$ is a benzene ring substituted with a halogen and an alkoxy group.

Another embodiment of the present invention are compounds of formula I, wherein $Ar_1$ is a benzene ring substituted with 1 to 3 alkoxy groups and $Ar_2$ is a substituted indole ring.

Another embodiment of the present invention are compounds of formula I, wherein $Ar_1$ is a benzene ring substituted with 1 to 3 alkoxy groups and $Ar_2$ is a substituted benzimidazole ring.

Another embodiment of the present invention is a compound of Formula II:

wherein $R_a$, $Ar_{1-3}$, and $Z_{1-3}$ are the same as defined above for formula I.

Another embodiment of the present invention is a compound of Formula III:

wherein $R_a$, $Ar_{1-3}$, and $Z_{1-3}$ are the same as defined above for formula I.

Another embodiment of the present invention is a compound of Formula IV:

wherein $R_a$, $Ar_{1-3}$, and $Z_{1-3}$ are the same as defined above for formula I.

Another embodiment of the present invention are the compounds of Formula V:

wherein $R'_1$ and $R'_2$ are independently selected from:

OH, $NH_2$, $OCH_3$, $N(CH_3)2$, $CH_2OH$, $CH_2NH_2$, $CH_2OCH_3$, and $CH_2N(CH_3)_2$.

Another embodiment of the present invention are the following compounds:

T116

T117

T118

T119

Substituents $R'_3$, $R'_4$, and $R'_5$ in T117, T118, and T119 are independently selected from hydrogen and hydrogen bond donor groups containing oxygen and nitrogen, such as hydroxyl, unsubstituted amino, and monoalkylamino.

It is to be understood that this invention covers all appropriate combinations of the particular and preferred groupings referred to herein.

The compounds of this invention may be prepared by employing procedures known in the literature starting from known compounds or readily prepared intermediates. Exemplary general procedures follow.

Compounds of formula I can be prepared according to the following scheme, wherein the variables are as described above, excepting those variables which one skilled in the art would appreciate would be incongruent with the method described.

Scheme I.

As depicted above in Scheme I, 3,4,5-trimethoxyl benzoyl chloride is added slowly to 1.0 equivalent of amine solution, which is dissolved in chloroform, and mixed with 1.0 equivalent triethylamine at 0-5° C. After the reaction is complete, the chloroform solution is extracted three times by water and concentrated under vacuum. The amide precipitates immediately when the concentrated syrup is cooled to room temperature. The amide purity is sufficient to be used directly for the next step.

Amide is then dissolved in anhydrous chloroform, and 1.05 equivalent Lawesson's Reagent is added at room temperature. The solution is heated to 62° C. under inert gas. The color of the chloroform solution yellows slowly. After the reaction is complete, the product is purified by column chromatography using ethyl acetate and hexane as developing solvents.

The yellow thioamide is suspended in anhydrous alcohol under inert gas atmosphere. With vigorous stirring, the reactants are cooled to 0° C., and 5.0 equivalent of anhydrous hydrazine is slowly added, after which the thioamide is stirred at room temperature, preferably overnight. The alcohol and unreacted hydrazine are then evaporated under vacuum. The syrup is then dissolved in chloroform and extracted by water three times. The organic layer is dried and concentrated under vacuum. The resulting amidrozone is a white solid.

The amidrozone is dissolved in alcohol. 5.0 equivalent of trimethyl orthoformate is then added at room temperature. Several drops of sulfuric acid are added as a catalyst, and the solution is stirred vigorously for 2 hours. After neutralization, the alcohol is evaporated and a compound of formula I is purified by column chromatography using ethyl acetate and hexane as developing solvents.

The compounds of formula I can be included in pharmaceutical compositions to treat, for example, a pathology linked to a hyperproliferative disorder in a patient. Such pathologies include, but are not limited to, restenosis, inflammation, and cancers susceptible to treatment by inhibition of mitotic spindle formation, such as leukemia, lung cancer, colon cancer, central nervous system cancer, ovarian cancer, renal cancer, breast cancer, cervical cancer, prostate cancer, bladder cancer, liver cancer, lymphoma, pancreatic cancer, thyroid cancer, Kaposi's sarcoma, and malignant melanoma.

Therefore, also provided is a pharmaceutical composition comprising a pharmaceutically effective amount of the compound of formula I and a pharmaceutically acceptable carrier.

In practice, a composition containing a compound of formula I may be administered in any variety of suitable forms, for example, by inhalation, topically, parenterally, rectally or orally. More specific routes of administration include intravenous, intramuscular, subcutaneous, intraocular, intrasynovial, colonical, peritoneal, transepithelial including transdermal, ophthalmic, sublingual, buccal, dermal, ocular, nasal inhalation via insufflation, and aerosol.

A composition containing a compound of formula I may be presented in forms permitting administration by the most suitable route. The invention also relates to administering compositions containing a compound of formula I, which is suitable for use as a medicament in a patient. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of oral dosage forms, or injectable solutions, or suspensions.

The choice of vehicle and the compound of formula I in the vehicle are generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used. In addition, the compound of formula I may be incorporated into sustained-release preparations and formulations.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of the compound of formula I as a free base or pharmacologically acceptable salt can be prepared in water suitably mixed with a surfactant such as hydroxypropyl-cellulose. Dispersion can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, and/or by various antibacterial and antifungal agents, for example, parabens, chlorobutanol, phenol, sorbic acid, thimerosal, and the like.

Sterile injectable solutions are prepared by incorporating the compound of formula I in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

Topical administration, gels (water or alcohol based), creams or ointments containing the compound of formula I may be used. The compound of formula I may be also incorporated in a gel or matrix base for application in a patch, which would allow a controlled release of compound through transdermal barrier.

For administration by inhalation, the compound of formula I inhibitor may be dissolved or suspended in a suitable carrier for use in a nebulizer or a suspension or solution aerosol, or may be absorbed or adsorbed onto a suitable solid carrier for use in a dry powder inhaler.

Compositions according to the invention may also be formulated in a manner which resists rapid clearance from the vascular (arterial or venous) wall by convection and/or diffusion, thereby increasing the residence time of the particles at the desired site of action. A periadventitial depot comprising a compound according to the invention may be used for sustained release. One such useful depot for administering a compound according to the invention may be a copolymer matrix, such as ethylene-vinyl acetate, or a polyvinyl alcohol gel surrounded by a Silastic shell. Alternatively, a compound according to the invention may be delivered locally from a silicone polymer implanted in the adventitia.

An alternative approach for minimizing washout of a compound according to the invention during percutaneous, transvascular delivery comprises the use of nondiffusible, drug-eluting microparticles. The microparticles may be comprised of a variety of synthetic polymers, such as polylactide for example, or natural substances, including proteins or polysaccharides. Such microparticles enable strategic manipulation of variables including total dose of drug and kinetics of its release. Microparticles can be injected efficiently into the arterial or venous wall through a porous balloon catheter or a balloon over stent, and are retained in the vascular wall and the periadventitial tissue for at least about two weeks. Formulations and methodologies for local, intravascular site-specific delivery of therapeutic agents are discussed in Reissen et al. (Am. C'oll. Cardial. 1994 ; 23: 1234-1244), the entire contents of which are hereby incorporated by reference.

A composition according to the invention may also comprise a hydrogel which is prepared from any biocompatible or non-cytotoxic (homo or hetero) polymer, such as a hydrophilic polyacrylic acid polymer that can act as a drug absorbing sponge. Such polymers have been described, for example, in application W093/08845, the entire contents of which are hereby incorporated by reference. Certain of them, such as, in particular, those obtained from ethylene and/or propylene oxide are commercially available.

In the use of compounds according to the invention for treating pathologies which are linked to hyperproliferative disorders, the compounds according to the invention can be administered in different ways. For the treatment of restenosis, the compounds of the invention are administered directly to the blood vessel wall by means of an angioplasty balloon, which is coated with a hydrophilic film (for example a hydrogel) which is saturated with the compound, or by means of any other catheter containing an infusion chamber for the compound, which can thus be applied in a precise manner to the site to be treated and allow-the compound to be liberated locally and efficiently at the location of the cells to be treated. This method of administration advantageously makes it possible for the compound to contact quickly the cells in need of treatment.

The treatment method of the invention preferably consists in introducing a compound according to the invention at the site to be treated. For example, a hydrogel containing composition can be deposited directly onto the surface of the tissue to be treated, for example during a surgical intervention.

Advantageously, the hydrogel is introduced at the desired intravascular site by coating a catheter, for example a balloon catheter, and delivery to the vascular wall, preferably at the time of angioplasty. In a particularly advantageous manner, the saturated hydrogel is introduced at the site to be treated by means of a balloon catheter. The balloon may be chaperoned by a protective sheath as the catheter is advanced toward the target vessel, in order to minimize drug washoff after the catheter is introduced into the bloodstream.

Another embodiment of the invention provides for a compound according to the invention to be administered by means of perfusion balloons. These perfusion balloons, which make it possible to maintain a blood flow and thus to decrease the risks of ischaemia of the myocardium, on inflation of the balloon, also enable the compound to be delivered locally at normal pressure for a relatively long time, more than twenty minutes, which may be necessary for its optimal action. Alternatively, a channeled balloon catheter ("channeled balloon angioplasty catheter", Mansfield Medical, Boston Scientific Corp., Watertown, Mass.) may be used. The latter consists of a conventional balloon covered with a layer of 24 perforated channels, which perfuse via an independent lumen through an additional infusion orifice.

Various types of balloon catheters, such as double balloon, porous balloon, microporous balloon, channel balloon, balloon over stent and hydrogel catheter, all of which may be used to practice the invention, are disclosed in Reissen et al. (1994), the entire contents of which are hereby incorporated by reference.

The use of a perfusion balloon catheter is especially advantageous, as it has the advantages of both keeping the balloon inflated for a longer period of time by retaining the properties of facilitated sliding and of site-specificity of the hydrogel are gained simultaneously.

Another aspect of the present invention relates to a pharmaceutical composition comprising a compound according to the invention and poloxamer, such as Poloxamer 407 is a non-toxic, biocompatible polyol, commercially available (BASF, Parsippany, N.J.).

A poloxamer impregnated with a compound according to the invention may be deposited directly on the surface of the tissue to be treated, for example during a surgical intervention. Poloxamer possesses essentially the same advantages as hydrogel while having a lower viscosity.

The use of a channel balloon catheter with a poloxamer impregnated with a compound according to the invention is especially advantageous. In this case, the advantages of both keeping the balloon inflated for a longer period of time while retaining the properties of facilitated sliding, and of site specificity of the poloxamer, are gained simultaneously.

The compounds of the present invention may also be formulated for use in conjunction with other therapeutic agents such as agents or in connection with the application of therapeutic techniques to address pharmacological conditions, which may be ameliorated through the application of a compound of formula I, such as in the following:

The compounds of the present invention may be used in the treatment of restenosis post angioplasty using any device such as balloon, ablation, or laser techniques.

The compounds of the present invention may be used in the treatment of restenosis following stent placement in the vasculature either as 1) primary treatment for vascular blockage, or 2) in the instance where angioplasty using any device fails to give a patent artery.

The compounds of the present invention may be used either orally, by parenteral administration or the compound could be applied topically through the intervention of a specific device or as a properly formulated coating on a stent device.

In one aspect, the coating on a stent device is formed by applying polymeric material in which the compound of the invention is incorporated to at least one surface of the stent device.

Polymeric materials suitable for incorporating the compound of the invention include polymers having relatively low processing temperatures such as polycaprolactone, poly (ethylene-co-vinyl acetate) or poly (vinyl acetate or silicone gum rubber and polymers having similar relatively low processing temperatures. Other suitable polymers include non-degradable polymers capable of carrying and delivering therapeutic drugs such as latexes, urethanes, polysiloxanes, styrene-ethylene/butylene-styrene block copolymers (SEBS) and biodegradable, bioabsorbable polymers capable of carrying and delivering therapeutic drugs, such as poly-DL-lactic acid (DL-PLA), and poly-L-lactic acid (L-PLA), polyolthoesters, polyiminocarbonates, aliphatic polycarbonates, and polyphosphazenes.

A porosigen may also be incorporated in the drug-loaded polymer by adding the porosigen to the polymer along with the therapeutic drug to form a porous drug-loaded polymeric membrane.

"Porosigen" means as any moiety, such as microgranules of sodium chloride, lactose, or sodium heparin, for example, which will dissolve or otherwise be degraded when immersed in body fluids to leave behind a porous network in the polymeric material. The pores left by such porosignes can typically be as large as 10 microns. The pores formed by porosignes such as polyethylene glycol (PEG), polyethylene oxide/polypropylene oxide (PEO/PPO) copolymers, for example, can also be smaller than one micron, although other similar materials which form phase separations from the continuous drug loaded polymeric matrix and can later be leached out by body fluids can also be suitable for forming pores smaller than one micron. The polymeric material can be applied to the stent while the therapeutic drug and porosigen material are contained within the polymeric material, to allow the porosigen to be dissolved or degraded by body fluids when the stent is placed in a blood vessel, or alternatively, the porosigen can be dissolved and removed from the polymeric material to form pores in the polymeric material prior to placement of the polymeric material combined with the stent within a blood vessel.

If desired, a rate-controlling membrane can also be applied over the drug loaded polymer, to limit the release rate of the compound of the invention. The rate-controlling membrane can be added by applying a coating form a solution, or a lamination. The rate-controlling membrane applied over the polymeric material can be formed to include a uniform dispersion of a porosigen in the rate-controlling membrane, and the porosigen in the rate-controlling membrane can be dissolved to leave pores in the rate-controlling membrane typically as large as 10 microns, or as small as 1 micron, for example, although the pores can also be smaller than 1 micron. The porosigen in the rate-controlling membrane can be, for example sodium chloride, lactose, sodium heparin, polyethylene glycol, polyethylene oxide/polypropylene oxide copolymers, or mixtures thereof.

In another aspect, the coating on the stent device can be formed by applying the compound of the invention to at least one surface of the stent device to form a bioactive layer and then applying one or more coats of porous polymeric material over the bioactive layer, such that the porous polymeric material has a thickness adequate to provide a controlled release of the compound.

In one aspect, the porous polymeric material is composed of a polyamide, parylene or a parylene derivative applied by catalyst-free vapor desposition. "Parylene" refers to a polymer based on p-xylylene and made by vapor phase polymerization as described in U.S. Pat. No. 5,824,049, incorporated herein by reference.

Alternatively, the porous polymeric material is applied by plasma deposition. Representative polymers suitable for plasma deposition include poly (ethylene oxide), poly (ethylene glycol), poly (propylene oxide), and polymers of methane, silicone, tetrafluoroethylene tetramethyldisiloxane, and the like.

Other suitable polymer systems include polymers derived from photopolymerizable monomers such as liquid monomers preferably having at least two cross linkable C—C (Carbon to Carbon) double bonds, and being a non-gaseous addition polymerizable ethylenically unsaturated compound, having a boiling point above 100° C., at atmospheric pressure, a molecular weight of about 100-1500 and being capable of forming high molecular weight addition polymers readily. More preferably, the monomer is preferably an addition photopolymerizable polyethylenically unsaturated acrylic or methacrylic acid ester containing two or more acrylate or methacrylate groups per molecule or mixtures thereof.

Representative examples of such multifunctional acrylates are ethylene glycol diacrylate, ethylene glycol dimethacrylate, trimethylopropane triacrylate, trimethylopropane trimethacrylate, pentaerythritol tetraacrylate, or pentaerythritol tetramethacrylate. 1 amides of (meth) acrylic acid, such as N-methylol methacrylamide butyl ether are also suitable, N-vinyl compounds such as N-vinyl pyrrolidone, vinyl esters of aliphatic monocarboxylic acids such as vinyl oleate, vinyl ethers of diols such as butanediol-1-1,4-divinyl ether and allyl ether and allyl ester are also suitable. Also included are other monomers such as the reaction products of di- or polyepoxides such as butanediol-1-1, 4-diglycidyl ether or bisphenol A diglycidyl ether with (meth) acrylic acid. The characteristics of the photopolymerizable liquid dispersing medium can be modified for the specific purpose by a suitable selection of monomers or mixtures thereof.

Other useful polymer systems include a polymer that is biocompatible and minimizes irritation to the vessel wall when the stent is implanted. The polymer may be either a biostable or a bioabsorbable polymer depending on the desired rate of release or the desired degree of polymer stability. Bioabsorbable polymers that could be used include poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D, L-lactic acid), poly(glycolic acidcotrimethylene carbonate), polyphosphoester, polyphosphoester urethane, poly(amino acids), cyanoacrylates, poly (trimethylene carbonate), poly(iminocarbonate), copoly (ether-esters) (e.g., PEO/PLA), polyalkylene oxlates, polyphoosphazenes and biomolecules such as fibrin, fibrinogen, cellulose, starch, collagen and hyaluronic acid. Also, biostable polymers with a relatively low chronic tissue response such as polyurethanes, silicones, and polyesters could be used and other polymers could also be used if they can be dissolved and cured or polymerized on the stent such as polyolefins, polyisobutylene and ethylene-alphaolefine copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones, polyvinyl aromatics, such as polystyrene, polyvinyl esters, such as polyvinyl acetate; copolymers of vinyl monomers with each other and olefins, such as ethylene-methyl methacrylate copolymers, acrylonitril-styrene copolyers, ABS resins, and ethylene-vinyl acetate copolymers; polyamides, such as Nylone 66 and polycaprolactam; alkyl reins, polycarbonates; polyoxymethylenes; polyimides, polyethers; epoxy reins, polyurethanes; rayon; rayon-triacetate; cellulose, cellulose acetate, cellulose butyrate; cellulose acetate buryrate; cellophane, cellulose nitrate; cellulose propionate; cellulose ethers; and carboxymethyl cellulose.

In addition to plasma deposition and vapor phase deposition, other techniques for applying the various coatings on the stent surfaces may be employed. For example, a polymer solution may be applied to the stent and the solvent allowed to evaporate, thereby leaving on the stent surface a coating of the polymer and the therapeutic substance. Typically, the solution can be applied to the stent by either spraying the solution onto the stent or immersing the stent in the solution.

The compounds of the present invention may be used in the treatment of restenosis in combination with any anticoagulant, antiplatelet, antithrombotic or profibrinolytic agent. Often patients are concurrently treated prior, during and after interventional procedures with agents of these classes either in order to safely perform the interventional procedure or to prevent deleterious effects of thrombus formation. Some examples of classes of agents known to be anticoagulant, antiplatelet, antithrombotic or profibrinolytic agents include any formulation of heparin, low molecular weight heparins, pentasaccharides, fibrinogen receptor antagonists, thrombin inhibitors, Factor Xa inhibitors, or Factor VIIa inhibitors.

The compounds of the present invention may be used in combination with any antihypertensive agent or cholesterol or lipid-regulating agent in the treatment of restenosis or atherosclerosis concurrently with the treatment of high blood pressure or atherosclerosis. Some examples of agents that are useful in the treatment of high blood pressure include compounds of the following classes: beta-blockers, ACE inhibitors, calcium channel antagonists and alpha-receptor antagonists. Some examples of agents that are useful in the treatment of elevated cholesterol levels or disregulated lipid levels include compounds known to be HMGCoA reductase inhibitors and compounds of the fibrate class.

The compounds of the present invention may be used in the treatment of various forms of cancer either alone or in combination with compounds known to be useful in the treatment of cancer.

The percentage of compound of formula I in the compositions used in the present invention may be varied, it being necessary that it should constitute a proportion such that a suitable dosage shall be obtained. Obviously, several unit dosage forms may be administered at about the same time. A dose employed may be determined by a physician or qualified medical professional, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 10, mg/kg body weight per day by intravenous administration. In each particular case, the doses are determined in accordance with the factors distinctive to the patient to be treated, such as age, weight, general state of health and other characteristics, which can influence the efficacy of the compound according to the invention.

The compound of formula I used in the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the compound of formula I may be administered 1 to 4 times per day. Of course, for other patients, it will be necessary to prescribe not more than one or two doses per day.

The following non-limiting examples set forth hereinbelow illustrate certain aspects of the invention.

EXAMPLES

Example 1

3-(3,4,5-trimethoxyl)phenyl-4-(4-methoxyl)phenyl-1,2,4(H)triazole (T111)

T111

Compound T111 was prepared according to Scheme 1. The following physical data was obtained: $^1$H NMR (400 MHz, CDCl$_3$), δ: 3.64 (s, 6H), 3.84 (d, 6H), 6.70 (s, 2H), 6.98 (d, 2H), 7.19 (d, 2H), 8.25 (s, 1H); MS (ESI): m/z=342 (M$^+$+1); Anal. (C$_{18}$H$_{19}$O$_4$N$_3$) C, H, O, N; mp: 163-165° C.

Example 2

3-(3,4,5-trimethoxyl)phenyl-4-(N,N-dimethylamino)phenyl-1,2,4(H)triazole (T112)

T112

Compound T112 was prepared according to Scheme 1. The following physical data was obtained: $^1$H NMR (400 MHz, CDCl$_3$), δ: 2.99 (s, 6H), 3.65 (s, 6H), 3.83 (s, 3H), 6.71 (d, 2H), 6.76 (s, 2H), 7.09 (d, 2H), 8.22 (s, 1H); MS (ESI): m/z=355 (M$^+$+1); Anal. (C$_{19}$H$_{20}$O$_3$N$_4$) C, H, O, N; mp: 145-147° C.

Example 3

3-(3,4,5-trimethoxyl)phenyl-4-(3-hydroxyl, 4-methoxyl)phenyl-1,2,4(H)triazole (T113)

Compound T113 was prepared according to Scheme 1. The following physical data was obtained: $^1$H NMR (400 MHz, CDCl$_3$), δ: 3.66 (s, 6H), 3.83 (s, 3H), 3.94 (s, 3H), 6.18 (s, 1H), 6.74 (m, 3H), 6.89 (m, 2H), 8.24 (s, 1H); MS (ESI): m/z=358 (M$^+$+1); Anal. (C$_{18}$H$_{19}$O$_5$N$_3$) C, H, O, N; mp: 197-198° C.

Example 4

3-(3,4,5-trimethoxyl)phenyl-4-(3-fluoro, 4-methoxyl)phenyl-1,2,4(H)triazole (T114)

Compound T114 was prepared according to Scheme 1. The following physical data was obtained: $^1$H NMR (400 MHz, CDCl$_3$), δ: 3.67 (s,6H), 3.89 (s, 3H), 3.93 (s, 3H), 3.69 (s, 2H), 7.05 (in, 3H), 8.25(s, 1H); MS(ESI): m/z=360 (M$^+$+1); Anal. (C$_{18}$H$_{18}$O$_4$N$_3$F) C, H, O, N, F; mp: 151-152° C.

Example 5

3-(3,4,5-trimethoxyl)phenyl-4-(N-methyl-6-(1H) indolyl)-1,2,4(H)triazole (T115)

Compound T115 was prepared according to Scheme 1. The following physical data was obtained: $^1$H NMR (400 MHz, CDCl$_3$), δ: 3.52 (s, 6H), 3.80 (s, 3H), 3.84 (s, 3H), 6.51 (s, 1H), 6.73 (s, 2H), 7.04 (d, 1H), 7.17 (s, 1H), 7.37 (d, 1H), 7.559 (s, 1H), 8.30(s, 1H); MS (ESI): m/z=365 (M$^+$+1); Anal. (C$_{20}$H$_{20}$O$_3$N$_3$) C, H, O, N; mp: 157-159° C.

Determination of Biological Activity

Figure 1:
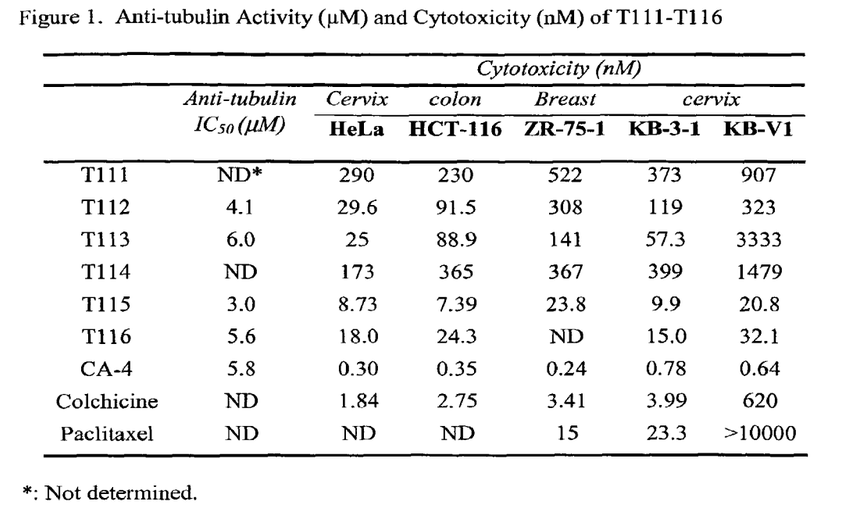
FIG. 1 is a table providing the anti-tubulin activity (µM) and cytotoxicity (nM) values for T111-T116.

T112, TI 13, T115 and T116 demonstrate apparent inhibitory constants (IC$_{50}$s) similar to those observed for known inhibitors (FIG. 1). Tubulin polymerization assays were conducted using the CytoDYNAMIX Screen™ 03 (Cytoskeleton Inc., CO.) assay system following the manufacturer's instructions. Tubulin (>99% pure, Cat #TL238) was reconstituted to 3 mg/ml using G-PEM buffer (80 mM PIPES pH 6.8, 0.5 mM EGTA, 2.0 mM MgCl$_2$, 1.0 mM GTP plus 5% glycerol). 100 μl of the reconstituted tubulin was added to each well of a pre-warmed 96-well plate. The tubulin polymerized efficiently at 37° C. reaching a maximum OD$_{340\,nm}$ of approximately 0.12 in 50 minutes (3000 seconds). Compounds were added at varying concentrations (ranging from 0.03-30 μM) and their effects on polymerization determined over a period of 60 minutes. The absorbance at OD$_{340\,nm}$ was recorded every 60 sec. using a TECAN GENios multifunction microplate reader (TECAN U.S. Inc., Research Triangle Park, N.C.) at 37° C. Apparent IC$_{50}$ inhibitory values for the compounds were determined by a non-linear regression analysis with Prism 3.03 (Graphpad Software Inc., San Diego, Calif.) using area under curve (AUC) for the polymerization profiles.

Figure 2:
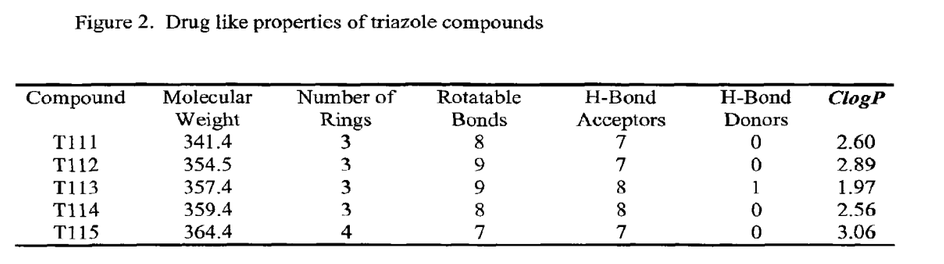
FIG. 2 is a table illustrating the drug-like properties of triazole compounds.

In vivo drug effects require that a compound be readily absorbed into cells and maintained at therapeutic but not toxic doses. A measure of a compound's bioavailability can be estimated using values of the hydrophobic/hydrophilic balance, as measured by logP, and the compounds molecular weight. Calculated log P values were predicted using the C log P program (Daylight Chemical Information Systems, Santa Fe, N. Mex.) and the molecular weight of a compound can be readily calculated as the sum of the weights of the individual atoms. A study by Lipinski et al. (Experimental and computational approaches to estimate solubility and permeability in drug discovery and developmental setting, Adv. Drug Del. Rev. 23, 3-25 (1997).) has shown that a value of ClogP ≤5 and a molecular weight ≤500 Daltons are exhibited by 'orally available druglike' compounds. Other "drug like" properties include: 0-5 hydrogen bond donor atoms; 5-10 hydrogen bond acceptor atoms; 1-4 rings; and 2-8 rotatable bonds. All compound tested adhere to these "rules of thumb" for drug-likeness (FIG. 2).

Figure 3:
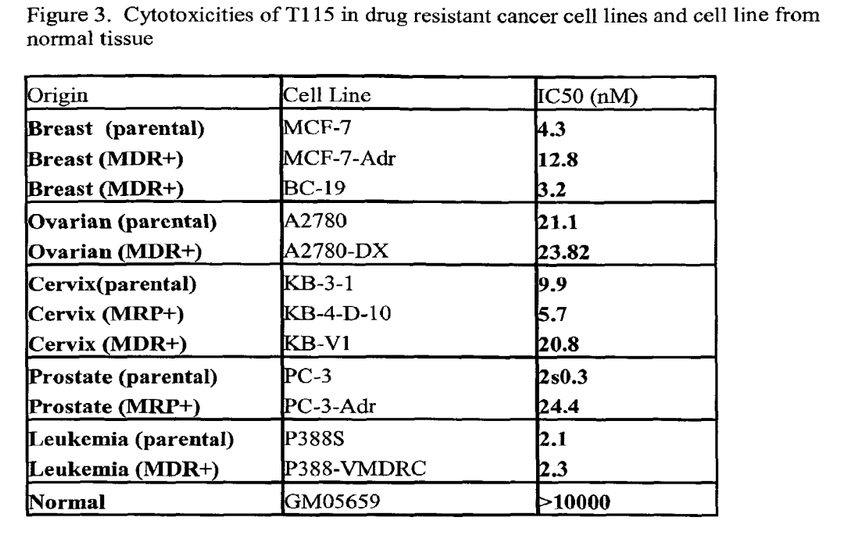
FIG. 3 is a table providing the cytotoxicities of T115 in drug resistant cancer cell lines and cell line from normal tissue.

The cytotoxic effects of the compounds were examined using human cervix epithelial adenocarcinoma cell line (HeLa), human breast carcinoma cell line (ZR-75-1), human colon carcinoma cell line (HCT116), human cervix carcinoma cell line (KB-3-1) and its multiple drug resistance (MDR+) subclone (KB-V1) (FIG. 1). A further cytotoxic evaluation of T115 was also performed using major cancer cell lines and their drug resistant derivatives (FIG. 3). The cells were maintained at 37° C., 5% $CO_2$ atmosphere in humidified incubator. Cells in logarithmic phase were diluted to a density of 20000-60000 cells/ml in culture media based on growth characteristics. For each well of a 96-well microplate, 100 μL cell dilution was seeded and allowed to attach overnight, then exposed to varying concentrations ($10^{-5}$-$10^{-12}$M) of compounds for 72-hours (37° C., 5% $CO_2$ atmosphere). The cells were stained with 0.5 mg/ml MTT (3-(4, 5-dimethylthiazolyl-2)-2,5-diphenyltetrazoliym bromide) and incubated at culture condition for 3 hours. After the media were removed, 150 μl DMSO was added into each well to dissolve the purple crystals and the absorbance of the solutions at $OD_{595\ nm}$ was recorded. Compounds were tested in triplicate in least three independent assays. The $IC_{50}$ values were determined by a non-linear regression analysis using Prism 3.03 (Graphpad Software Inc., San Diego, Calif.). Average values are reported here (FIGS. 1 and 3).

A detailed evaluation of cancer cell growth inhibition effect for T111-T115 was conducted by the NIH-National Center Institute (NCI) Developmental Therapeutic Program (DTP) (FIG. 4). A large negative number denotes stronger activity. For example, compound T115 exhibits exceptionally strong activity against EKVX (<-8.00), NCI-H322M (<-8.00), NCI-H522 (<-8.00) cells associated with non-small cell lung cancer. Overall, T115 performed uniformly well across the 60-cell line panel.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A method for treating restenosis or a hyperproliferative disorder selected from the group consisting of restenosis, leukemia, lung cancer, colon cancer, central nervous system cancer, ovarian cancer, renal cancer, breast cancer, cervical cancer, prostate cancer, bladder cancer, liver cancer, lymphoma, pancreatic cancer, thyroid cancer, Kaposi's sarcoma, and malignant melanoma, said method comprising administering to a patient in need thereof an anti-mitotic effective amount of the compound of formula (I):

wherein

Het is a substituted 1,2,4-triazole;

$Z_1 Z_2$, and $Z_3$ are independently a bond or $R_1$—X—$R_2$, wherein X is $NR_3$, O, S, SO, or $SO_2$; $R_1$ and $R_2$ are independently a bond or substituted or unsubstituted, saturated or unsaturated, straight-chained or branched lower alkylene; and $R_3$ is hydrogen, substituted or unsubstituted phenyl, or substituted or unsubstituted, saturated or unsaturated, straight-chained or branched lower alkyl;

$Ar_1$ is substituted monocyclic aryl;

$Ar_2$ is substituted or wisubstituted indolyl;

$R_a$ is hydrogen or a substituted or unsubstituted monocyclic, aryl, or heteroaryl ring system of 5 or 6 ring atoms or a bicyclic aryl or heterotnyl ring system of 8 to 12 ring atoms, wherein each monocyclic ring may contain 0 to 3 heteroatoms, each bicyclic ring may contain 0 to 4 heteroatoms, and each heteroatom is independently selected from the group consisting of N, O, and S; and the substituents of $Ar_1$, $Ar_2$, and $R_a$, when substituted, comprise one to three moieties independently selected from the group consisting of alkyl, alkenyl, alkynyl, phenyl, aralkyl, aralkenyl, hydroxy, hydroxyalkyl, alkoxy, alkoxyalkyl, aralkoxy, aryloxy, acyloxy, halo, haloalkyl, nitro, cyano, amino, mono- and dialkylamino, acylamino, carboxy, carboxyalkyl, carbalkoxy, carbaralkoxy, carbalkoxyalkyl, carbalkoxyalkenyl, aminoalkoxy, amido, mono-alkylamido, di-alkylamido, N,N-cycloaLkylamido, sulfonyl, mono-alkyl sulfonyl, di-alkyl sulfonyl, sulthmoyl, monoalkyl sulfamoyl, di-alkyl sulfamoyl, halophenyl, benzoyl, alkylthio and alkylsulfmyl; or a pharmaceutically acceptable salt thereof.

2. The method according to claim 1, for the treatment of restenosis.

3. The method according to claim 1, wherein said hyperproliferarive disorder is at a site of mechanical injury to an arterial wall produced by treatment of an atherosclerotic lesion by angioplasty.

4. The method according to claim 1, wherein said hyperproliferative disorder is a cancer susceptible to treatment by inhibition of mitotic spindle formation.

5. The method according to claim 1 for the treatment of a proliferateive disorder selected from the group consisting of leukemia, lung cancer, colon cancer, central nervous system cancer, ovarian cancer, renal cancer, breast cancer, cervical cancer, and prostate cancer, bladder cancer, liver cancer, lymphoma, pancreatic cancer, thyroid cancer, Kaposi's sarcoma, and malignant melanoma.

6. The method according to claim 1, wherein $Ar_1$ is substituted benzene, and $Ar_2$, is substituted or unsubstituted indole.

7. The method according to claim 1, wherein $R_a$ is a substituted or unsubstituted aromatic ring selected from the group consisting of benzene, pyrrole, thiophene, furan, thiazole, imidazole, pyrazole, 1,2,4-triazole, pyridine, 2(1H)-pyridone, 4(1-H)pyridone, pyrazine, pyrimidine, pyridazine, isothiazole, isoxazole, oxazole, tetrazole, naphthalene, tetralin, naphthyridine, benzofuran, benzothiopheric, indole, 2,3dihydroindole, 1H-indazole, indoline, benzopyrazole, 1,3-benzodioxole, benzoxazole, purine, coumarin, chromone, quinoline, tetrahydroquinoline, isoquinoline, benzimidazole, quinazoline, pyrido[2,3-b]pyrazine, pyrido[3,4-b]pyrazine, pyrido[3,2-c]pyridazine, pyrido[3,4-b]-pyridine, 1H-pyrazole[3,4-d]pyrimidine, pteridine, 2(1H)-quinolone, 1(2H)-isoquinolone, 1,4-benzisoxazine, benzothiazole, quinoxaline, quinoline-N-oxide, isoquinoline-N-oxide, quinoxaline-N-oxide, quinazoline-N-oxide, benzoxazine, phthalazine, and cinnoline.

8. The method according to claim 1, wherein each $Z_1$, $Z_2$, and $Z_3$ is a bond, $Ar_1$ is a substituted benzene, and $R_a$, is hydrogen.

9. The method according to claim 8, wherein $Ar_1$ is substituted with 1 to 3 alkoxy groups.

10. The method according to claim 8, wherein $Ar_1$ is substituted with 1 to 3 alkoxy groups, and $Ar^2$ is substituted with 1 to 3 substituents independently selected from hydroxyl, amino, and monoalkylamino groups.

11. The method according to claim 1, wherein the compound of formula (I) has the formula:

12. The method according to claim 1, wherein the compound of formula (I) has the formula:

13. The method according to claim 1, wherein $Z_1$, $Z_2$, and $Z_3$ are each independently a bond, and the compound of formula (I) is further characterized by formula:

wherein R is hydrogen, hydroxyl, amino, or monoalkylamino.

14. The method according to claim 13, wherein R is hydrogen.

15. The method according to claim 1, wherein $Z_1$, $Z_2$, and $Z_3$ are each independently a bond, and the compound of formula (I) is further characterized by formula:

wherein R is hychogen. hydroxyl, amino or monoalkylamino.

16. The method according to claim 15, wherein R is hydrogen.

17. The method according to claim 1, wherein $Z_1$, $Z_2$, and $Z_3$ are each independently a bond, and the compound of formula (1) is further characterized by formula:

wherein $R_1$ and $R_2$ are independently selected from the group consisting of hydrogen, —OH, —NH$_2$, —OCH$_3$, —N(CH$_3$)$_2$, —CH$_2$OH, —CH$_2$OCH$_3$, —CH$_2$N(CH$_3$)$_2$,

* * * * *